Figure 2:
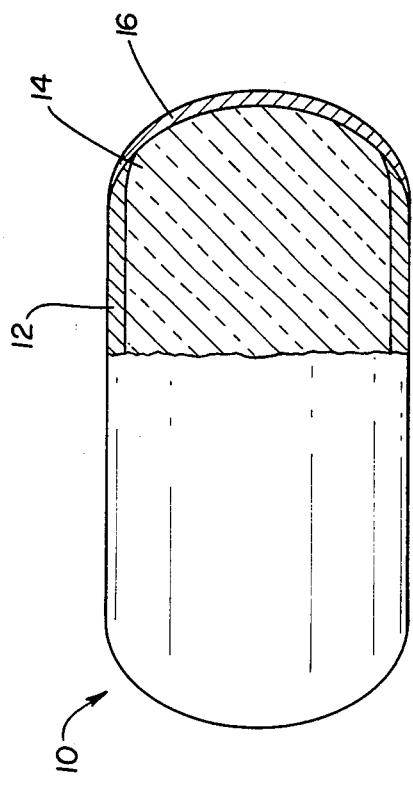

United States Patent [19]
Wu et al.

[11] Patent Number: 4,717,567
[45] Date of Patent: Jan. 5, 1988

[54] RUMEN-STABLE PELLETS
[75] Inventors: Stephen H. Wu; Edward G. Miller, Jr., both of Kingsport, Tenn.
[73] Assignee: Eastman Kodak Company, Rochester, N.Y.
[21] Appl. No.: 802,102
[22] Filed: Nov. 25, 1985
[51] Int. Cl.⁴ .......................... A61K 9/22; A61K 9/24
[52] U.S. Cl. ...................................... 424/462; 424/482
[58] Field of Search ................... 424/33, 31, 462, 482; 604/890, 892

[56] References Cited
U.S. PATENT DOCUMENTS

| | | | |
|---|---|---|---|
| T 100,404 | 3/1981 | Wu | 424/482 |
| 4,181,710 | 1/1980 | Dannelly et al. | 424/33 |
| 4,196,187 | 4/1980 | Dannelly et al. | 424/482 |
| 4,459,279 | 7/1984 | Stricker et al. | 424/33 |
| 4,503,030 | 3/1985 | Edgren et al. | 424/15 |
| 4,519,801 | 5/1985 | Edgren | 604/890 |
| 4,522,625 | 6/1985 | Edgren | 604/890 |
| 4,601,893 | 7/1986 | Cardinal | 424/15 |
| 4,618,487 | 10/1986 | Du Bois et al. | 604/890 |

FOREIGN PATENT DOCUMENTS

| | | |
|---|---|---|
| EP77264 | 4/1983 | European Pat. Off. . |
| EP148811 | 7/1985 | European Pat. Off. .............. 424/33 |
| 57258 | 4/1946 | Netherlands . |
| WO84/04657 | 12/1984 | PCT Int'l Appl. . |
| 1098006 | 1/1968 | United Kingdom . |
| 1372040 | 10/1974 | United Kingdom . |
| 2020181 | 11/1979 | United Kingdom . |

Primary Examiner—Ronald W. Griffin
Attorney, Agent, or Firm—John F. Stevens; William P. Heath, Jr.

[57] ABSTRACT

Disclosed are coatings for protecting pellet cores from environmental conditions of predetermined pH conditions. The coatings have a pH sensitive portion and a pH insensitive portion. The pH sensitive portion allows the cores to be protected by the coating under certain pH conditions and disintegrates under other pH conditions to allow exposure of the cores.

9 Claims, 3 Drawing Figures

U.S. Patent   Jan. 5, 1988   4,717,567

RUMEN-STABLE PELLETS

TECHNICAL FIELD

This invention relates in general to pellets adapted to be orally administered to ruminants and which are beneficial to ruminants after passing the rumen and reaching the abomasum and/or intestines. More particularly, this invention relates to pellets having, in terms of structure, a core material such as a nutrient or medicament, and a coating over the core material which protects the core in the environment of the rumen, but which loses continuity under the more acidic conditions of the abomasum to render the core material available for utilization by the animal.

BACKGROUND OF THE INVENTION

In ruminants, ingested feed first passes into the rumen, where it is pre-digested or degraded by fermentation. During this period of fermentation the ingested feed may be regurgitated to the mouth where it is salivated and masticated. After a period of fermentation regulated by natural processes and variable depending on the animal and the feedstuff, absorption of digested nutrients starts and continues in the subsequent sections of the digestive tract by the ruminant animal. This process is described in detail by D. C. Church, "Digestive Physiology and Nutrition of Ruminants", Vol. 1, O.S.U. Book Stores, Inc., of Corvallis, Oreg.

The rumen, the largest of the four stomach compartments of ruminants, serves as an important location for metabolic breakdown of ingested foodstuffs through the action of microorganisms which are present therein. Ingested food is typically retained in the rumen for from about 6 to 30 hours during which time it is subject to metabolic breakdown by the rumen microorganisms. Much ingested protein material is broken down in the rumen to soluble peptides and amino acids and utilized by the rumen microorganisms. When the rumen contents pass into the abomasum and intestine, the microbial mass is digested, thus providing protein to the ruminant. Thus, the natural nutritional balance of the ruminant animal is primarily a function of the microbial composition and population.

In preparing nutrients and medicaments intended for administration to ruminants, it is important to protect the active ingredients against the environmental conditions of the rumen, i.e., microbial degradation and the effects of a pH of about 5.5, so the active substance will be saved until it reaches the particular location where absorption takes place. It is well known that the rate of meat, wool and/or milk production can be increased if sources of growth limiting essential amino acids, and/or medicaments, are protected from alteration by microorganisms residing in the rumen and become available for direct absorption by the animal later in the gastrointestinal tract.

Materials which protect the core against degradation by the rumen contents should be resistant to attack by the rumen fluid which contains enzymes or microorganisms but must make the active ingredient available rapidly in the more acidic fluid of the abomasum at a pH within the normal physiological range of about 2 to about 3.5. To more easily coat or encapsulate active ingredients in protective materials, the protective materials should be soluble in certain organic solvents for coating purposes.

Because proteins are subject to breakdown in the rumen, it has been suggested that protein-containing nutrients fed to ruminants be treated so as to permit passage without microbial breakdown through the rumen to the abomasum. Suggested procedures have included coating the protein material, for example, with fats and vegetable oils; heat treating of the protein material; reacting the protein material with various compounds such as formaldehyde, acetylenic esters, polymerized unsaturated carboxylic acid or anhydrides and phosphonitrilic halides, etc.

It is well known that all proteins found in animal and plant life are chemical compounds containing different combinations of over 20 amino acids, the number and arrangement of such acids being fixed in any particular protein. Twelve of these amino acids can be synthesized in nutritonally adequate amounts from other substances by biochemical processes normally present in most animals, but the remaining 10 essential amino acids are not synthesized in sufficient quantities and must be ingested by the animal. Since the proportions of the constituent amino acids in a particular protein cannot be varied, the essential amino acid least in supply limits the amounts of that protein which can be produced by the animal. Consequently, for any given diet, there will be a particular essential amino acid which limits the production of protein incorporating that essential amino acid unless, of course, two or more such amino acids are equally limiting.

The application of the above principles leads to the formulation of diets for nonruminant animals which provide the optimum proportion of amino acids and have enabled significant increases in protein production to be achieved. In the ruminant, dietary proteins and amino acids are, to a variable extent, broken down to ammonia and various organic compounds by microbial fermentation in the first two compartments of the stomach (the rumen and reticulum). The bacteria and protozoa in these organs utilize these metabolites for their own growth and multiplication and the microbial protein so formed passes on to the abomasum, the compartment of the stomach corresponding to the stomach of nonruminants, where it is partially digested. The process is completed in the small intestine and the amino acids are absorbed.

It is likewise well-known that medicaments are more effective when they are protected from the environment of the rumen. See, for example, U.S. Pat. Nos. 3,041,243 and 3,697,640.

Of interest is U.S. Pat. No. 4,177,255 which discloses a polymeric matrix having a substance dispersed therein which is stable in the rumen but leachable from the matrix postruminally. This patent discloses that the matrix is continuous. From this, it is concluded that there is no alignment of the dispersed substance forming a continuous path entirely through the coating.

Also of interest is published European Application No. 77,264 which discloses a coating obtained by combining a copolymer sensitive to variations in pH with a polymer insensitive to variations in pH and optionally an organic acid, the second polymer improving the liberation of the active substance at a pH between 1 and 2.5 and decreasing is extractability in aqueous media.

Other U.S. patents of interest which disclose rumen stable coating compositions comprising a polymer having basic amino groups and one or more substances dispersed therein include U.S. Pat. Nos. 4,181,708, 4,181,709 and 4,181,710. The present invention provides a coating for protecting a core of a material beneficial to ruminants (e.g., nutrients, medicament, etc.). The coating consists of a pH insensitive portion and a pH sensitive portion, allowing the core to be exposed in a predetermined environment.

Sometimes, pH sensitive coating materials are more expensive than pH insensitive, and the present invention therefore provides a more economical coating. Also, pH sensitive coatings are sometimes more subject to mechanical damage during processing of animal feed materials which obviously destroys their utility. The present invention therefore provides for a more versatile coating which may result in a more economical coating which is more resistant to mechanical damage from processing equipment.

DISCLOSURE OF INVENTION

According to the present invention, there is provided a capsule suitable for oral administration to ruminant animals having
 (a) a core comprising a substance beneficial to ruminant animals postruminally, and
 (b) a shell enclosing said core, said shell comprising
  (1) a first portion of a physiologically acceptable film-forming material having at least one area of discontinuity, said first portion being resistant to mechanical damage by conventional handling and processing techniques and stable in the environment of the rumen for a period of at least 30 hours, and
  (2) a second portion occupying the discontinuity in said first portion, said second portion comprising a substance different from said first portion which is also stable in the environment of the rumen for a period of at least 30 hours, but which loses its integrity postruminally within about 6 hours.

The core is of a material beneficial to the ruminant upon passing the rumen and reaching the abomasum and/or intestine. Normally, the core is a solid material which has been formed into particles, such as by pelletizing. The cores may then be rounded, if desired, by conventional means, such as by tumbling. The core should have sufficient body or consistency to remain intact during handling, particularly during the coating operation. Suitable core materials include various medicaments and nutrients such as, for example, antibiotics, relaxants, drugs, anti-parasites, amino acids, proteins, sugars, carbohydrates, mixtures thereof, etc. The core may also contain inert filler material such as clay.

Some amino acids suitable for use as a core material, their pH and solubility are as follows: lysine, alanine, asparagine, arginine, cystine, methionine, leucine, tyrosine, and phenylalanine.

Proteins from various sources are valuable for practice of the invention. Generally, proteins are polymers derived from various combinations of amino acids. Proteins are amphoteric substances which are soluble or suspendable in aqueous media either more acidic or more basic that the particular protein being considered.

The core material may be made ready for coating by the following method. The nutrient, medicament or the like is mixed with water, binder, and sometimes inert inorganic substances added to adjust the specific gravity of the pellet and the resulting plastic dough-like mass is extruded or rolled to obtain suitable size particles. Adhesive binders may be added to strengthen the pellet and can be nontoxic vegetable gums, starches, cellulose derivatives, animal gums and other similar substances well-known in the art of food thickening and tablet making. Inorganic additives used to adjust the pH or the specific gravity of the pellet include such substancs as insoluble, nontoxic pigment-like materials such as metal sulfates, silicates, oxides and carbonates having a relatively high density. The final desirable range of specific gravity for the rumen protected pellets is from 1.05 to 1.6. Afer creating suitable size pellets by extrusion, rolling or other suitable means, the pellets are dried to remove the water. The pellets are then coated.

Figure 3:
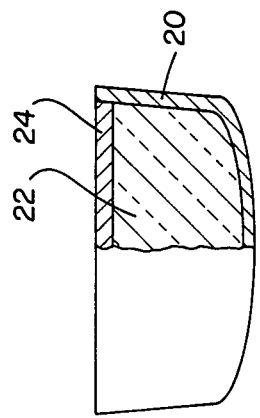
Figure 1:
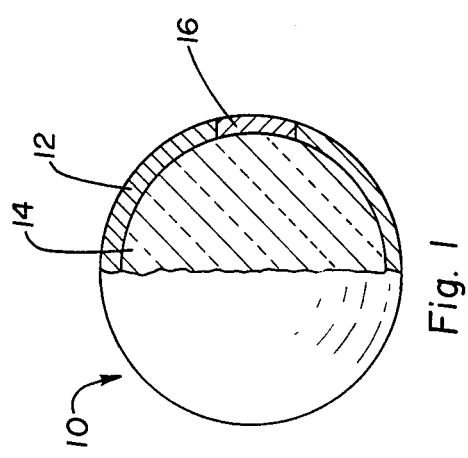

The invention is illustrated in the drawings, wherein:

FIG. 1 illustrates a generally spherical capsule according to this invention;

FIG. 2 illustates a generally cylindrical capsule having rounded ends according to this invention; and FIG. 3 illustrates another shape of a capsule according to this invention wherein a preformed cup-like member is filled with core material and capped with a layer of pH sensitive material.

In FIGS. 1 and 2, the shell of the capsule 10, includes a first portion 12 of a physiologically acceptable material which has at least one area of discontinuity, that is, which has at least one hole or area exposing a portion of the core 14. This first portion is rumen stable, i.e., has the ability to remain intact in the environment of the rumen for a period of at least 30 hours and may be stable in the environment of the entire digestive tract. It also is resistant to mechanical damage (breakage, crushing, etc.) by conventional handling and processing techniques (mixing, packaging, etc.).

The second portion 16 of the shell occupies the discontinuity in the first portion, and comprises a substance different from the first portion and which is stable in the environment of the rumen at a pH above about 5 for 6 to 30 hours, but which loses its integrity in the environment of the abomasum or intestines (postruminally) at a pH below about 3.5 within about 6 hours. Thus, the second portion is effective to form a passageway directly to the core from the outside upon losing its integrity.

In FIG. 3, a preformed cup-like structure 20 is of a pH insensitive material (first portion) having a filling of core material 22. The core material in this embodiment may be loose and powder-like. A cover layer, or second portion 24 is of a pH sensitive material as described herein. The cup-like structures may be produced by, for example, thermoforming, then filled and covered with the second portion 24 by apparatus known in the art.

The useful substances for the first portion of the shell include at least one polymer, copolymer, or blend of polymers selected from polystyrene, poly(methyl methacrylate), poly(vinylchloride), copolymers of vinylidene chloride, poly(dimethylsiloxane), cellulose esters, polyesters made from dicarboxylic acids having from about 8 to about 22 carbon atoms and glycols of about 4 to about 16 carbon atoms, polyamides from amino acids having from about 8 to about 22 carbon atoms or from dicarboxylic acids having from about 8 to about 22 carbon atoms condensed with diamines having from about 4 to about 16 carbon atoms and polymethacrylates having silicone or fluorine substituted alcohol moieties or from 2 to 8 carbon atoms. Polystyrene and poly(methyl methacrylate) are preferred.

The acid-sensitive, organic or inorganic substances useful as a material for the second portion of the shell include nontoxic multivalent cation salts of phosphoric and phosphorous acids such as magnesium phosphate, basic magnesium phosphate, aluminum phosphate, magnesium phosphite, ferrous phosphate, ferric phosphate and calcium phosphate. Useful organic materials include the general categories of polymers containing from 3 to 14% nitrogen as basic amino groups, particles of polyelectrolyte complexes wherein a polymer containing basic amino groups is linked to a high molecular weight acid and preferably an acidic polymer to form an insoluble, pulverizable composition, particles of polyelectrolyte complexes wherein an acidic polymer is linked to a high molecular weight amine and preferably an amino group containing polymer, and a multivalent cationic salt of an acidic polymer. This portion of the shell may also contain plasticizers, inert fillers, etc.

More specifically, the polymers useful in forming the second portion of the shell include basic nitrogen-containing polymers, copolymers, or blends of polymers selected from cellulose derivatives such as cellulose propionate morpholinobutyrate; polymers containing addition-type monomeric moieties such as acrylonitrile; vinylated derivatives of pyridine; amides of methacrylic acid or acrylic acid such as a dialkylmino ethyl acrylate or methacrylate in which the alkyl group contains from 1 to 6 carbon atoms; vinyl substituted heterocylic ring or condensed ring compounds containing basic nitrogen configurations such as vinyl carbazole, vinyl quinoline, N-vinylpyrrole and 5-vinyl pyrozoline; polyamide-type polymers containing basic nitrogen not reacted in the polymerization process; and other basic nitrogen containing polymers such as preformed polymers which have been formed by reacting an existing polymer with a nitrogen-containing organic or inorganic moiety such as polybutadiene to which ammonia has been reacted with the remaining double bond. Especially preferred are poly(vinylpyridine), polymeric derivatives of vinylpyridine, and the copolymers of the various isomers and derivatives of vinylpyridine copolymerized with one or more of the above-mentioned addition type monomers.

Also, especially preferred as the material for the second portion are copolymers of 2-vinylpyridine and styrene, and in particular, the copolymer of about 75–85% by weight 2-vinylpyridine and about 15–25% by weight styrene, as well as the copolymer of 55–65% by weight 2-vinylpyridine and about 35–45% by weight acrylonitrile. These copolymers are commercially available or may be produced by conventional techniques well known in the art. The substances described above preferably have dispersed therein hydrophobic substances and/or certain inert materials. The hydrophobic substances include waxes, resins, polymers, fatty acids having from 12 to 32 carbon atoms, aluminum salts of fatty acids having from 12 to 32 carbon atoms, and polyfunctional carboxylic acids having a ratio of from 10 to 22 carbon atoms per carboxyl group and a molecular weight of from 400 to 1000.

The inert materials include metal flake, mineral flake, crosslinked organic polymer, etc. (e.g., aluminum flake, talc, graphite and ground mica). Such materials should have a size range of about 100 micron to 1 micron. Suitable coating compositions comprising polymers, hydrophobic substances and flake materials are described in U.S. Pat. Nos. 4,181,708; 4,181,709; and 4,181,710, which are incorporated herein by reference.

The shell may be applied to the cores by any convenient means. For example, the cores may be partially coated by electrostatic powder coating, spraying from solvent solution, application of molten shell material, etc. The second portion of the shell may be applied in a separate operation, by the same means. Alternately, a sheet of material suitable for use as the first portion may be thermoformed such that a multiplicity of cavities are formed therein. Subsequently, these cavities may be filled with core material, and the second portion of the shell applied as a coating to complete the encapsulation of the core material. Subsequently, the individual capsules or pellets may be separated by cutting, breaking apart, etc.

The following examples are submitted for a better understanding of the invention. In the examples, the cores consist of methionine and sufficient binder for the pellets to be self-supporting during handling and the coating operation.

EXAMPLE 1

This example illustrates a capsule which is coated over about one-half its surface with cellulose acetate butyrate (first portion) and over the remainder of its surface with 2-vinyl pyridine/styrene (80/20) copolymer, which is a pH sensitive polymer.

The cellulose acetate butyrate is ground cryogenically to a particle size of $-150$ to $+350$ mesh. Cores to be coated are placed on an electrically grounded screen. Cellulose acetate butyrate powder is sprayed onto about half of the surface of the cores. The partially coated cores are exposed to solvent vapor (ethanol/trichloroethylene). Within 5 seconds, a continuous film is formed. The film dries quickly. The cores are then turned over to the side which is not coated with cellulose acetate butyrate. The second portion of the cores is sprayed with 2-vinylpyridine/styrene copolymer (80/20, I.V. =1.0) powder which has generally the same particle size as the cellulose acetate butyrate. The coated cores are again exposed to the same solvent. Thus, the cores are coated with one pH-sensitive polymer and a pH insensitive polymer. The coating is continuous so that adhesion is adequate. The cores are found to be protected against pH conditions of about 5.5 for 24 hours, and are released by the pH sensitive coating dissolving in pH environment of about 2.9 after about 1 hour.

EXAMPLE 2

Example 1 is repeated except that cellulose acetate (CA-400-25 marketed by Eastman Chemical Products, Inc.), a pH insensitive polymer, is used in place of the cellulose acetate butyrate. Cores coated with this combination are found to have similar protection-release characteristics to those of Example 1.

EXAMPLE 3

Example 1 is repeated, except that the first portion of the shell occupies about 95% of the surface area of the pellets and the second portion of the shell occupies about 5% of the surface area of the pellets. The second portion of the shell, however, extends entirely to the surface of the core, thereby forming a continuous path to the core when it dissolves. These cores are found to have similar protection-release characteristics as the half-and half shell of Example 1.

EXAMPLE 4 (Comparative Example)

Example 1 is repeated, except the entire surface of the cores is covered with 2-vinylpyridine/styrene copolymer (80/20). Coating weight is 14% of the total weight of the pellets. These pellets are found to be stable in the environment of the rumen (pH of 5.5) for 24 hours, but release the core material in the environment of the abomasum (pH of 2.9) in about 1 hour. This example illustrates that the shells of Examples 1-3 having only an area of pH sensitive shell, but which extends entirely to the surface of the core, have comparable protection-release characteristics to core coated generally with the pH sensitive material.

EXAMPLE 5

Example 1 is repeated using as the second portion of the shell, a mixture of about 30 wt. % 2-vinylpyridine copolymer (80-20), about 5 wt. % stearic acid, and about 65 wt. % talc. These shells resulted in protection at pH 5.5 for about 30 hours and releases at pH 2.9 within about 2 hours for about 90% of the pellets.

The fluid used to simulate environmental conditions of the rumen (at pH 5.5) is prepared by making 11.397 grams of sodium acetate with 1.322 grams of sodium acetate with 1.32 grams of acetic acid and diluting this mixture with demineralized water to 1 liter.

The fluid used to simulate environmental conditions of the abomasum (at pH 2.9) is prepared by mixing 7.505 grams glycine with 5.85 grams sodium chloride and diluting this mixture with demineralized water to 1 liter. Eight parts of this solution are mixed with 2 parts of 0.1 normal hydrochloric acid for the test fluid.

The fluids are found to give reliable results in testing the pellets, according to similar experiments using actual rumen and abomasum fluid withdrawn from a ruminant.

I.V. (inherent viscosity) herein is measured at 25° C. using 0.5 gram polymer per 100 ml of a solvent consisting of 60 wt. % phenol and 40 wt. % tetrachloroethane.

Unless otherwise specified, all ratios, percentages, etc., are by weight.

The invention has been described in detail with particular reference to certain preferred embodiments thereof, but it will be understood that variations and modifications can be effected within the spirit and scope of the invention.

We claim:

1. A capsule suitable for oral administration to ruminant animals having
    (a) a core comprising a substance beneficial to ruminant animals postruminally, and
    (b) a shell enclosing said core, said shell comprising
        (1) a first portion of a physiologically acceptable film-forming material having at least one area of discontinuity, said first portion being resistant to mechanical damage by conventional handling and processing techniques and stable in the environment of the rumen for a period of at least 30 hours, and
        (2) a second portion occupying the discontinuity in said first portion, said second portion comprising a substance different from said first portion which is also stable in the environment of the rumen for a period of at least 30 hours, but which loses its integrity postruminally within about 6 hours.

2. A capsule according to claim 1 wherein said second portion comprises a vinylpyridine polymer.

3. A capsule according to claim 1 wherein said second portion comprises a 2-vinylpyridine/styrene copolymer having about 60 to about 75% repeat units from 2-vinylpyridine and about 40 to about 25% repeat units from styrene.

4. A capsule according to claim 3 wherein said second portion comprises said copolymer and a hydrophobic substance.

5. A capsule according to claim 4 wherein said second portion comprises an inert material selected from metal flake, mineral flake, crosslinked organic polymer, graphite and mica.

6. A capsule according to claim 1 wherein said first portion comprises a cellulose ester.

7. A capsule according to claim 1 wherein said core comprises at least one amino acid.

8. A capsule according to claim 1 wherein said second portion extends over about 50% or less of the surface of the core.

9. A capsule according to claim 1 wherein said second portion extends over about 5% or less of the surface of the core.

* * * * *